United States Patent [19]

Zukosky et al.

[11] Patent Number: 4,616,064

[45] Date of Patent: Oct. 7, 1986

[54] POLYMERIC COMPOSITIONS SUITABLE FOR USE IN THE MEDICAL FIELD AND COMPRISING A THERMOPLASTIC OLEFIN, A SILOXANE POLYMER, AND AN ELASTOMER

[75] Inventors: Mimzee Zukosky, Redwood City; Ronald L. Dieck, Sunnyvale, both of Calif.

[73] Assignee: Raychem Corporation, Menlo Park, Calif.

[21] Appl. No.: 633,369

[22] Filed: Jul. 23, 1984

Related U.S. Application Data

[63] Continuation-in-part of Ser. No. 488,861, Apr. 26, 1983, Pat. No. 4,525,531.

[51] Int. Cl.[4] .................... C08L 53/02; C08L 67/02; C08L 77/00
[52] U.S. Cl. ........................................ 525/92; 525/89; 525/95; 525/101; 525/106; 525/131
[58] Field of Search .................. 525/92, 89, 101, 106, 525/63, 66, 131

[56] References Cited

U.S. PATENT DOCUMENTS

| | | | |
|---|---|---|---|
| 3,332,900 | 7/1967 | Reischl et al. | 525/66 |
| 3,664,959 | 5/1972 | Gaines et al. | 525/106 |
| 3,674,891 | 7/1972 | Wheeler | 525/106 |
| 4,350,795 | 9/1982 | Bohm et al. | 525/194 |

FOREIGN PATENT DOCUMENTS

| | | | |
|---|---|---|---|
| WO80/00061 | 1/1980 | PCT Int'l Appl. | |
| 2016482 | 9/1979 | United Kingdom | 525/92 |

*Primary Examiner*—Wilbert J. Briggs, Sr.
*Attorney, Agent, or Firm*—Timothy H. P. Richardson; Herbert G. Burkard

[57] ABSTRACT

Polymeric compositions comprising 7–28%, preferably 12 to 25%, of a thermoplastic olefin polymer, 1–10%, preferably 2 to 6%, of a siloxane polymer containing 2–70% of siloxane units and at least 20% by weight of carbonate, urethane or amide units, and 69 to 90%, preferably 72 to 83%, of an elastomer. The olefin polymer can for example be polyethylene, polypropylene, or a polar ethylene copolymer. The elastomer can be a thermoplastic elastomer, an ionomer, or a styrene/butadiene copolymer. The compositions are particularly useful in the medical field, for example in the form of tubing.

11 Claims, No Drawings

POLYMERIC COMPOSITIONS SUITABLE FOR USE IN THE MEDICAL FIELD AND COMPRISING A THERMOPLASTIC OLEFIN, A SILOXANE POLYMER, AND AN ELASTOMER

CROSS-REFERENCE TO RELATED APPLICATION

This application is a continuation-in-part of our copending application Ser. No. 488,861, filed Apr. 26, 1983, now U.S. Pat. No. 4,525,531, the disclosure of which is incorporated herein by reference.

BACKGROUND OF THE INVENTION

1. Field of the Invention

This invention relates to new polymeric compositions and their use as shaped products, especially in the medical field.

2. Introduction to the Invention

There is a need, especially in the field of human medicine, for polymeric compositions which have good tactile properties, including a low coefficient of friction with the human skin, e.g. for use in endotracheal tubes and other tubes for delivering or removing liquids from the body and for use as catheter shaft materials. It is also desirable that such compositions should not contain ingredients, e.g. plasticizers, which migrate into liquids contacting them, and that they should not absorb liquids contacting them. It is also desirable that such composition should be suitable for radiation sterilization.

SUMMARY OF THE INVENTION

The compositions of the invention comprise a polymeric composition which comprises, and in which the polymeric component preferably consists essentially of:
  (a) 5 to 40%, preferably 7 to 28%, of a thermoplastic polymer comprising units derived from an olefin,
  (b) 1 to 10% of a polymeric component consisting essentially of 2 to 70% by weight of siloxane units, and at least 20% by weight of other units which are connected into a polymer backbone through a carbonate, urethane or amide linkage, and
  (c) 55 to 94%, preferably 62 to 92%, of an elastomer having a Shore D Hardness of less than 60,
  the amounts of components (a), (b) and (c) being by weight, based on the total weight of (a), (b) and (c).
  [Percentages are by weight throughout this specification, except where otherwise noted.]

The novel compositions are particularly useful in the form of tubing and other articles which are to be contacted by nitroglycerine, especially such articles which contact the human skin, because they absorb substantially less nitroglycerin than known polymeric compositions and have excellent tactile properties. In addition, many of the compositions show substantially less spallation, e.g. when used for peristaltic pump tubing, than known compositions having otherwise similar properties. Other valuable uses of the new compositions are described below.

DETAILED DESCRIPTION OF THE INVENTION

The relative proportions of the polymers (a), (b) and (c) play an important part in determining the properties of the blends. The siloxane polymer (b) preferably provides 2 to 10%, particularly 2 to 6%, of the blend. In the absence of a sufficient quantity of the siloxane polymer (b), the composition is difficult to process and the polymers (a) and (c) do not become adequately mixed under normal processing conditions; in addition the tactile properties of the composition are unsatisfactory for many purposes, especially in the medical field. The thermoplastic polymer (a) preferably provides 12 to 25%, particularly 15 to 22%, of the blend. The elastomer (c) preferably provides 72 to 83% of the blend. When the composition is to be used for medical purposes, in which its tactile properties in contact with human skin or other living material is important, the blend preferably contains 15 to 25%, especially 17 to 22%, of polymer (a), 2 to 8% of polymer (b), and 67 to 85%, especially 70 to 81%, of polymer (c).

Suitable thermoplastic polymers for use as component (a) of the novel compositions include polyolefins, particularly polyethylene (low density, linear low density, medium density and high density) and polypropylene, and copolymers of olefins, particularly ethylene, with one or more polar comonomers, particularly vinyl acetate, ethyl acrylate, methyl acrylate and methyl methacrylate. The polymers of high crystallinity, e.g. at least 30% crystallinity, particularly isotactic polypropylene, are preferred for tubing and other articles which are to be contacted by nitroglycerin; in general, the higher the crystallinity, the less the absorption of nitroglycerin.

The polymeric component (b) is preferably a block copolymer, or a mixture of polymers in the form of an interpenetrating network; however, random copolymers can also be used. One preferred class of block copolymers comprises polysiloxane and polycarbonate blocks, e.g. poly(dimethylsiloxane) blocks and polycarbonate blocks, such as those sold by General Electric under the trade designations GE5530 and GE3320. Another very useful class of polymers comprise an interpenetrating network of a polysiloxane, e.g. a poly(dimethylsiloxane), e.g. 2 to 15%, and a polyurethane or a polyamide. The polyurethane can be of the aliphatic ether type (e.g. as in Rimplast PTUA102, which contains about 10% of a polysiloxane), or the aromatic ester type (e.g. as in Rimplast PTUE 1201, which contains about 8% of a polysiloxane), or the aromatic ether type, as in Rimplast PTUE302, which contains about 10% of a polysiloxane. Suitable interpenetrating polysiloxane/polyamides include Rimplast PTA 1201, wherein the polyamide is Nylon-12. These Rimplast polymers are sold by Petrarch Systems Inc. The polymeric component (b) is generally a solid at room temperature.

Suitable elastomers for use as component (c) of the novel compositions include the following polymers:
  (1) Ionomers, in particular the metal salts of ethylene/methacrylic acid copolymers sold by du Pont under the tradename "Surlyn". Ionomers usually have a Shore D hardness of about 40.
  (2) Styrene/butadiene copolymers, in particular polystyrene/polybutadiene/polystyrene block copolymers such as those sold under the trade names "Kraton" and "Solprene". Such polymers are substantially softer than those in category (1) above and usually have a Shore A hardness of 30 to 70.
  (3) Thermoplastic elastomers which consist essentially of a multiplicity of recurring short chain ester units and long chain ester units joined through ester linkages, said short chain ester units amounting to 15 to 75 percent by weight of said copolyester and being of the formula

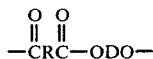

and said long chain ester units amounting to about 25 to 85 percent by weight of said copolyester and being of the formula

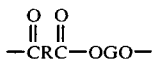

wherein R is the divalent aromatic radical remaining after removal of the carboxyl groups from aromatic dicarboxylic acid having a molecular weight of less than about 350, D is the divalent radical remaining after removal of the hydroxyl groups from organic diol having a molecular weight of less than 250, and G is the divalent radical remaining after removal of the terminal hydroxyl groups from a long chain glycol having an average molecular weight of 350 to 6000, said copolyester having a melt index of less than 150 and a melting point of at least 125° C., for example the polymers sold by du Pont under the trade name "Hytrel". Such polymers usually have a Shore D hardness of about 40.

(4) Amorphous polyamides, especially the higher polyamides such as Nylon-11 and Nylon-12, having a crystallinity less than 35%, particularly less than 20%. Such polymers usually have a Shore D hardness of about 40.

The various polymers and the amounts thereof can be selected to obtain compositions of preferred properties. We have found the invention to be particularly useful for producing compositions having at least one of the following properties:

(1) Low absorption of nitroglycerin (as discussed above).

(2) A tensile strength of 2,000 to 3,500 psi (140 to 245 kg/cm$^2$), e.g. 2,500 to 3,500 psi (175 to 345 kg/cm$^2$) and an elongation of 500 to 650%, preferably 500 to 625%; these compositions are similar to plasticized PVC in functional properties but do not contain plasticizer, which is liable to migrate. Such compositions can for example contain (1) 75 to 87% of a styrene/butadiene copolymer as defined above, e.g. Kraton G 2705, (2) 10 to 20% of polyethylene or an ethylene copolymer e.g. DFDA 6040, and (3) 3 to 10% of a polysiloxane/polycarbonate as defined above, e.g. GE 5530. These compositions can if desired by cross-linked by irradiation, using a dosage of up to 25 Mrad. Other such compositions can for example contain (1 ) 70 to 80% of a thermoplastic elastomer as defined above, e.g. Hytrel, (2) 15 to 25% of polyethylene, e.g. Marlex 6003, and (3) 3 to 10% of a polysiloxane/polycarbonate as defined above, e.g. GE 5530. These compositions can if desired be cross-linked by irradiation, using a dosage of for example up to 10 Mrad. Other such compositions can for example contain (1) 70 to 82% of a styrene/butadiene copolymer as defined above, e.g. Kraton G2705, (2) 15 to 22 % of polypropylene, preferably isotactic polypropylene, e.g. Profax 6523, and (3) 3 to 10% of a polysiloxane/polycarbonate, e.g. GE3320. These compositions can if desired be cross-linked by irradiation, using a dosage of for example 5 to 30 Mrad.

(3) A tensile strength of 550 to 1,500 psi (38.5 to 105 kg/cm$^2$), and an elongation of 360 to 480%; these compositions are similar to polysiloxanes in functional properties but are substantially cheaper. Such compositions can for example contain (1) 60 to 83% of a styrene/butadiene copolymer as defined above, particularly Kraton G2705, (2) 12 to 30%, e.g. 15 to 25%, of polypropylene, preferably isotactic polypropylene, e.g. Profax 62523, and (3) 3 to 10% of a polysiloxane/polycarbonate block coplymer as defined above, e.g. GE5530 or GE3320. Particularly when GE5530 is used, the composition can also contain a small amount, e.g. 2–5%, of a non-reinforcing filler. Other such compositions contain (1) 70 to 82% of an amorphous polyamide, e.g. Huels 4006, (2) 15 to 20% of polyethylene, preferably linear low density polyethylene, e.g. Sclair 8405, UV, and (3) 3 to 10% of a polysiloxane/polycarbonate block copolymer as defined above, e.g. GE3320. These compositions may desirably be cross-linked by irradiation, e.g. to a dose up to 30 Mrads, in order to arrive at a composition having optimum properties.

(4) A tensile strength of 1,000 to 2,000 psi (70 to 140 kg/cm$^2$) and an elongation of at least 650%; these compositions are similar to conventional "soft" elastomers but have improved tactile properties, especially for medical uses. Such compositions can for example contain (1) 70 to 82% of a thermoplastic elastomer as defined above, particularly Hytrel, (2) 15 to 20% of a copolymer of ethylene and a polar comonomer, e.g. vinyl acetate or ethyl acrylate, such as Elvax 460 or DPDA 6181 and (3) 3 to 10% of a polysiloxane/polycarbonate block copolymer, such as GE5530 or GE3320. These compositions may desirably be cross-linked by irradiation, e.g. to a dose up to 30 Mrads, preferably 10–25 Mrads, in order to arrive at a composition having optimum properties. Other such compositions can for example contain (1) 55–77% of a styrene-butadiene copolymer as defined above, particularly Kraton G2705, (2) 20 to 35% of polyethylene, preferably high density polyethylene, e.g. Marlex 6003, and (3) 3 to 10% of a polysiloxane/polycarbonate block copolymer such as GE3320.

The elongations and tensile strength referred to herein are measured by ASTM D-412 at room temperature and at a cross-head speed of 20 inches/minute.

The compositions of the inventions can be shaped in any desired way, preferably by melt-shaping, particularly melt-extrusion. The resulting shaped articles can be used as such, or, for a number of uses, can be cross-linked, preferably by radiation (usually after addition of at least 0.2%, preferably at least 0.3% of a radiation cross-linking agent such as triallyl isocyanurate). The cross-linking agent is usually added to the polymer blend before it is shaped. The cross-linked articles can be rendered heat-recoverable by deformation above the melting point of the thermoplastic polymer, followed by cooling in the deformed condition, as is well known.

The compositions of the invention can contain other ingredients such as antioxidants and other ingredients such as antioxidants and other stabilizers, fire-retardants, and conductive and non-conductive fillers. The compositions can also contain other polymers provided that they do not substantially detract from the valuable properties of the compositions.

EXAMPLES

The invention is illustrated in the following Examples, which are summarized in Tables 1-7 below. In each Example, the ingredients and the amounts thereof, in parts by weight, indicated in the Tables, and also (in each Example, though not given in the Table) 0.3 parts of an antioxidant and 1.5 parts of triallyl isocyanurate, were mixed together on a heated (170°-190° C.) mill, about 20-30% of the elastomer being added first, then the siloxane polymer, then about 70-80% of the olefin polymer, then the remainder of the elastomer, and finally the remainder of the olefin polymer. The mixture was stripped from the mill and pressed into slabs 6"×6" and about 25 mils thick. As noted in the Tables, some of the slabs were tested without crosslinking and others were tested after they had been "beamed" (i.e. exposed to electrons in a radiation beam) to a dose of 15 Mrad.

In the Tables below, the polymers are identified by their trade names; they have either been described already, in the earlier part of this specification, or are are further described below.

DPDA 6181 is an ethylene/ethyl acrylate copolymer.
MARLEX 6003 is a high density polyethylene.
SCLAIR 8405 UV is linear low density polyethylene.
ELVAX 460 is an ethylene/vinyl acetate copolymer.
GULF 2205 is an ethylene/methyl acrylate copolymer.

Siloxane Polymers

SWS 154 is a methyl vinyl siloxane free from fillers.
SWS 721 is a methyl vinyl siloxane containing a substantial proportion of fumed silica dispersed therein.
GE 5530 and GE 3320 are block copolymers of a polycarbonate and a dimethyl siloxane (see U.S. Pat. No. 3,189,662, the disclosure of which is incorporated by reference herein).

Elastomers

HUELS X 4003 is a Nylon 12.
HYTREL 4056 is a polyester elastomer as defined above, and
KRATON G 2705 is a polystyrene/polybutadiene/polystyrene elastomer.

TABLE 1

| EXAMPLE NO. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| PROFAX | 0 | 0 | 0 | 0 | 0 | 0 | 0 | 0 | 0 | 0 | 0 | 0 | 17 | 17 | 17 |
| DPDA 6181 | 0 | 0 | 0 | 0 | 0 | 0 | 0 | 0 | 0 | 17 | 17 | 17 | 0 | 0 | 0 |
| MARLEX 6003 | 0 | 0 | 0 | 0 | 0 | 0 | 17 | 17 | 17 | 0 | 0 | 0 | 0 | 0 | 0 |
| SCLAIR8405UV | 0 | 0 | 0 | 17 | 17 | 17 | 0 | 0 | 0 | 0 | 0 | 0 | 0 | 0 | 0 |
| ELVAX 460 | 17 | 17 | 17 | 0 | 0 | 0 | 0 | 0 | 0 | 0 | 0 | 0 | 0 | 0 | 0 |
| SWS 721 | 0 | 0 | 3 | 0 | 0 | 3 | 0 | 0 | 3 | 0 | 0 | 3 | 0 | 0 | 3 |
| GE 5530 | 0 | 3 | 0 | 0 | 3 | 0 | 0 | 3 | 0 | 0 | 3 | 0 | 0 | 3 | 0 |
| GE 3320 | 3 | 0 | 0 | 3 | 0 | 0 | 3 | 0 | 0 | 3 | 0 | 0 | 3 | 0 | 0 |
| KRATON G2705 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | | | | |
| TENSILE PSI | 1632 | 1584 | 1864 | 2490 | 2429 | 2564 | 2203 | 2309 | 2315 | 1452 | 1605 | 1478 | 2402 | 2642 | 2397 |
| % ELONGATION | 735 | 760 | 810 | 815 | 790 | 815 | 780 | 815 | 785 | 685 | 795 | 780 | 720 | 740 | 695 |
| BEAMED TEST DATA | | | | | | | | | | | | | | | |
| TENSILE PSI | | | | 1655 | 1692 | 1593 | 1507 | 1742 | 2359 | | | | 1358 | 1558 | 1306 |
| % ELONGATION | | | | 730 | 800+ | 780 | 630 | 730 | 720 | | | | 595 | 645 | 590 |
| M100 PSI | | | | 13 | 12 | 10 | 15 | 15 | 19 | | | | 1 | 0 | 0 |

TABLE 2

| EXAMPLE NO. | 16 | 17 | 18 | 19 | 20 | 21 | 22 | 23 | 24 | 25 | 26 | 27 |
|---|---|---|---|---|---|---|---|---|---|---|---|---|
| DPDA 6181 | 0 | 0 | 0 | 0 | 0 | 0 | 0 | 0 | 0 | 17 | 17 | 17 |
| MARLEX 6003 | 0 | 0 | 0 | 0 | 0 | 0 | 17 | 17 | 17 | 0 | 0 | 0 |
| SCLAIR8405UV | 0 | 0 | 0 | 17 | 17 | 17 | 0 | 0 | 0 | 0 | 0 | 0 |
| ELVAX 460 | 17 | 17 | 17 | 0 | 0 | 0 | 0 | 0 | 0 | 0 | 0 | 0 |
| SWS 721 | 0 | 0 | 3 | 0 | 0 | 3 | 0 | 0 | 3 | 0 | 0 | 3 |
| GE 5530 | 0 | 3 | 0 | 0 | 3 | 0 | 0 | 3 | 0 | 0 | 3 | 0 |
| GE 3320 | 3 | 0 | 0 | 3 | 0 | 0 | 3 | 0 | 0 | 3 | 0 | 0 |
| HYTREL | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | |
| TENSILE PSI | 2834 | 3765 | 3616 | 3137 | 2442 | 3692 | 2626 | 3140 | 3428 | 3035 | 2990 | 3047 |
| % ELONGATION | 775 | 850 | 845 | 855 | 740 | 885 | 720 | 830 | 815 | 775 | 770 | 765 |
| BEAMED TEST DATA | | | | | | | | | | | | |
| TENSILE PSI | 2127 | 2667 | 2617 | 2752 | 2506 | 3217 | 3575 | 4476 | 4057 | 2661 | 2771 | 2981 |
| % ELONGATION | 440 | 520 | 490 | 450 | 650 | 580 | 560 | 550 | 530 | 500 | 550 | 620 |
| M100 PSI | 56 | 60 | 66 | 56 | 55 | 50 | 70 | 55 | 52 | 47 | 40 | 49 |

Thermoplastic Polymers
PROFAX is isotactic polypropylene.

TABLE 3

| EXAMPLE NO. | 28 | 29 | 30 | 31 | 32 | 33 | 34 | 35 | 36 | 37 | 38 | 39 | 40 | 41 | 42 | 43 | 55 |
|---|---|---|---|---|---|---|---|---|---|---|---|---|---|---|---|---|---|
| PROFAX | 0 | 0 | 0 | 0 | 0 | 0 | 0 | 0 | 0 | 0 | 0 | 0 | 0 | 0 | 17 | 17 | 17 |
| KANEKA MMUS | 0 | 0 | 0 | 0 | 0 | 0 | 0 | 0 | 0 | 0 | 0 | 0 | 17 | 17 | 0 | 0 | 0 |
| DPDA 6181 | 0 | 0 | 0 | 0 | 0 | 0 | 0 | 0 | 0 | 17 | 17 | 17 | 0 | 0 | 0 | 0 | 0 |
| MARLEX 6003 | 0 | 0 | 0 | 0 | 0 | 0 | 17 | 17 | 17 | 0 | 0 | 0 | 0 | 0 | 0 | 0 | 0 |
| CLAIR8405UV | 0 | 0 | 0 | 17 | 17 | 17 | 0 | 0 | 0 | 0 | 0 | 0 | 0 | 0 | 0 | 0 | 0 |
| ELVAX 460 | 17 | 17 | 17 | 0 | 0 | 0 | 0 | 0 | 0 | 0 | 0 | 0 | 0 | 0 | 0 | 0 | 0 |
| SWS 721 | 0 | 0 | 3 | 0 | 0 | 3 | 0 | 0 | 3 | 0 | 0 | 3 | 0 | 0 | 0 | 0 | 3 |

TABLE 3-continued

| EXAMPLE NO. | 28 | 29 | 30 | 31 | 32 | 33 | 34 | 35 | 36 | 37 | 38 | 39 | 40 | 41 | 42 | 43 | 55 |
|---|---|---|---|---|---|---|---|---|---|---|---|---|---|---|---|---|---|
| GE 5530 | 0 | 3 | 0 | 0 | 3 | 0 | 0 | 3 | 0 | 0 | 3 | 0 | 0 | 3 | 0 | 3 | 0 |
| GE 3320 | 3 | 0 | 0 | 3 | 0 | 0 | 3 | 0 | 0 | 3 | 0 | 0 | 3 | 0 | 3 | 0 | 0 |
| HUELS 4006 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 | 78.2 |
| UNBEAMED TEST DATA | | | | | | | | | | | | | | | | | |
| TENSILE PSI | 1041 | 1193 | 1194 | 1119 | 1082 | 1383 | 1167 | 1282 | 1386 | 1046 | 1353 | 1279 | 1200 | 1117 | 975 | 892 | 1286 |
| % ELONGATION | 195 | 270 | 400 | 135 | 5 | 445 | 20 | 155 | 335 | 315 | 450 | 400 | 116 | 145 | 60 | 150 | 215 |
| BEAMED TEST DATA | | | | | | | | | | | | | | | | | |
| TENSILE PSI | 1621 | 1705 | 2440 | 1200 | 1944 | 1128 | 1576 | 2348 | 2193 | 111 | 2058 | 2201 | | | 1626 | 1613 | 1575 |
| % ELONGATION | 220 | 250 | 340 | 70 | 270 | 70 | 100 | 220 | 300 | 200 | 250 | 360 | | | 25 | 60 | 45 |
| M100 PSI | 51 | 74 | 62 | 58 | 65 | 51 | 58 | 47 | 59 | 46 | 50 | 48 | | | 40 | 44 | 6 |

TABLE 4

| EXAMPLE NO. | 45 | 46 | 47 | 48 | 49 | 50 | 51 | 52 |
|---|---|---|---|---|---|---|---|---|
| PROFAX | 0 | 0 | 0 | 0 | 0 | 17 | 17 | 17 |
| AESNO-TL | 0 | 0 | 0 | 17 | 17 | 0 | 0 | 0 |
| KANEKA MMBS | 17 | 17 | 17 | 0 | 0 | 0 | 0 | 0 |
| SWS 721 | 0 | 0 | 3 | 0 | 0 | 0 | 0 | 3 |
| GE 5530 | 0 | 3 | 0 | 0 | 3 | 0 | 3 | 0 |
| GE 3320 | 3 | 0 | 0 | 3 | 0 | 3 | 0 | 0 |
| HYTREL | 78.2 | 78.2 | 78.2 | 78.2 | 78.2 | 78.2 | 78.2 | 78.2 |
| UNBEAMED TEST DATA | | | | | | | | |
| TENSILE PSI | 2590 | 2581 | 2024 | 2171 | 2343 | 2021 | 2600 | 2092 |
| % ELONGATION | 620 | 580 | 510 | 580 | 640 | 625 | 765 | 580 |
| BEAMED TEST DATA | | | | | | | | |
| TENSILE PSI | | | | 1840 | 3527 | 1804 | 2639 | 3522 |
| % ELONGATION | | | | 460 | 430 | 425 | 800+ | 615 |
| M100 PSI | | | | 75 | 69 | 31 | 26 | 34 |

TABLE 5

| EXAMPLE NO. | 53 | 54 | 55 | 56 | 57 | 58 | 59 | 60 | 61 | 62 | 63 | 64 | 65 | 66 |
|---|---|---|---|---|---|---|---|---|---|---|---|---|---|---|
| MARLEX 6003 | 17 | 15 | 20 | 25 | 30 | 35 | 18.5 | 18.5 | 18.5 | 0 | 0 | 0 | 0 | 0 |
| DFD 6040 | 0 | 0 | 0 | 0 | 0 | 0 | 0 | 0 | 0 | 17 | 17 | 17 | 17 | 17 |
| SWS 721 | 0 | 0 | 0 | 0 | 0 | 0 | 0 | 0 | 0 | 3 | 0 | 0 | 0 | 0 |
| GE 5530 | 6 | 3 | 3 | 3 | 3 | 6 | 0 | 0 | 0 | 0 | 3 | 0 | 3 | 3 |
| GE 3320 | 0 | 0 | 0 | 0 | 0 | 0 | 0 | 0 | 0 | 0 | 0 | 3 | 0 | 0 |
| HYTREL | 75.2 | 80.2 | 75.8 | 70.2 | 65.2 | 57.2 | 79.7 | 0 | 0 | 78.2 | 78.2 | 78.2 | 0 | 0 |
| KRATON G2705 | 0 | 0 | 0 | 0 | 0 | 0 | 0 | 79.7 | 0 | 0 | 0 | 0 | 78.2 | 0 |
| HUELS 4006 | 0 | 0 | 0 | 0 | 0 | 0 | 0 | 0 | 79.7 | 0 | 0 | 0 | 0 | 78.2 |
| UNBEAMED TEST DATA | | | | | | | | | | | | | | |
| TENSILE PSI | 3427 | 3024 | 2774 | 2672 | 2622 | 1429 | 2703 | 2917 | 4960 | 3299 | 3710 | 3377 | 1812 | 1472 |
| % ELONGATION | 845 | 795 | 750 | 775 | 785 | 630 | 770 | 855 | 400 | 880 | 870 | 820 | 760 | 515 |
| BEAMED TEST DATA | | | | | | | | | | | | | | |
| TENSILE PSI | 2744 | 3216 | 2903 | 2707 | 2767 | 2725 | 3414 | 1781 | 4299 | 3804 | 3204 | 3015 | 1526 | 2313 |
| % ELONGATION | 535 | 590 | 550 | 465 | 475 | 400 | 560 | 690 | 325 | 690 | 655 | 615 | 755 | 300 |
| M100 PSI | 61 | 65 | 64 | 61 | 67 | 64 | 75 | 18 | 62 | 49 | 46 | 47 | 9 | 40 |

TABLE 6

| EXAMPLE NO. | 67 | 68 | 69 | 70 | 71 | 72 | 73 | 74 | 75 | 76 |
|---|---|---|---|---|---|---|---|---|---|---|
| MARLEX 6003 | 17 | 17 | 15 | 15 | 20 | 20 | 25 | 25 | 30 | 30 |
| GE 5530 | 6 | 6 | 3 | 3 | 3 | 3 | 3 | 3 | 3 | 3 |
| KRATON G2705 | 75.2 | 0 | 80.2 | 0 | 75.2 | 0 | 70.2 | 0 | 65.2 | 0 |
| HUELS 4006 | 0 | 75.2 | 0 | 80.2 | 0 | 75.2 | 0 | 70.2 | 0 | 65.2 |
| UNBEAMED TEST DATA | | | | | | | | | | |
| TENSILE PSI | 2281 | 1101 | 2800 | 1338 | 2360 | NA | 2436 | NA | 2950 | NA |
| % ELONGATION | 765 | 0 | 845 | 385 | 705 | 0 | 780 | 0 | 815 | 0 |
| BEAMED TEST DATA | | | | | | | | | | |
| TENSILE PSI | 1466 | 1601 | 1552 | 2140 | 1649 | 1600 | 2100 | 1677 | 1969 | 1381 |
| % ELONGATION | 715 | 110 | 745 | 280 | 810 | 0 | 740 | 0 | 680 | 0 |
| M100 PSI | 8 | 46 | 8 | 44 | 9 | NA | 14 | NA | 13 | NA |

TABLE 7

| EXAMPLE NO. | 77 | 78 | 79 | 80 | 81 | 82 | 83 | 84 | 85 | 86 | 87 | 88 |
|---|---|---|---|---|---|---|---|---|---|---|---|---|
| MARLEX 6003 | 0 | 0 | 0 | 0 | 17 | 0 | 0 | 0 | 0 | 0 | 0 | 0 |
| DED 6040 | 0 | 0 | 0 | 0 | 0 | 17 | 0 | 0 | 0 | 17 | 17 | 17 |
| GULF 2205 | 0 | 0 | 0 | 0 | 0 | 0 | 17 | 17 | 17 | 0 | 0 | 0 |
| SWS C154 | 0 | 0 | 0 | 0 | 0 | 0 | 0 | 0 | 0 | 3 | 3 | 3 |
| GE 5530 | 0 | 0 | 0 | 0 | 3 | 3 | 3 | 3 | 3 | 0 | 0 | 0 |

TABLE 7-continued

| EXAMPLE NO. | 77 | 78 | 79 | 80 | 81 | 82 | 83 | 84 | 85 | 86 | 87 | 88 |
|---|---|---|---|---|---|---|---|---|---|---|---|---|
| HYTREL | 0 | 98.2 | 0 | 0 | 0 | 0 | 78.2 | 0 | 0 | 78.2 | 0 | 0 |
| KRATON G2705 | 0 | 0 | 98.2 | 0 | 0 | 0 | 0 | 0 | 78.2 | 0 | 0 | 78.2 |
| HUELS 4006 | 98.2 | 0 | 0 | 0 | 0 | 0 | 0 | 78.2 | 0 | 0 | 78.2 | 0 |
| SURLYN AD9231 | 0 | 0 | 0 | 98.2 | 78.2 | 78.2 | 0 | 0 | 0 | 0 | 0 | 0 |
| UNBEAMED TEST DATA | | | | | | | | | | | | |
| TENSILE PSI | 2800 | 3847 | 1995 | 4255 | 4233 | 3823 | 4080 | 1491 | 1527 | 3520 | 1368 | 2000 |
| % ELONGATION | 655 | 800 | 825 | 430 | 670 | 435 | 840 | 465 | 760 | 820 | 440 | 770 |
| BEAMED TEST DATA | | | | | | | | | | | | |
| TENSILE PSI | 3127 | 5768 | 1434 | 5043 | 5485 | 4445 | 3704 | 2269 | 1433 | 3753 | 2513 | 1621 |
| % ELONGATION | 430 | 725 | 860 | 290 | 330 | 280 | 595 | 330 | 765 | 660 | 370 | 740 |
| M100 PSI | 34 | 21 | 0 | 60 | 61 | 78 | 34 | 39 | 4 | 32 | 33 | 8 |

TABLE 8

| Example No. | 89 | 90 | 91 | 92 |
|---|---|---|---|---|
| Kraton G2705 | 78 | 78 | 78 | 78 |
| Profax 6523 | 17 | 17 | 17 | 17 |
| PTUA 102 | 3 | — | — | — |
| PTUE 302 | — | 3 | — | — |
| PTA 1201 | — | — | 3 | — |
| PTUE 202 | — | — | — | 3 |
| UNBEAMED TEST DATA | | | | |
| Tensile (psi) | 2700 | 3300 | 2200 | 1800 |
| Elongation (%) | 680 | 550 | 800 | 790 |
| BEAMED TEST DATA | | | | |
| Tensile (psi) | 2000 | 2500 | 1900 | 1150 |
| Elongation (%) | 520 | 640 | 700 | 540 |

The blend of Example 92 was also beamed to 5, 10 and 20 Mrads with the following results

| Dose | 5 | 10 | 20 |
|---|---|---|---|
| Tensile (psi) | 1500 | 1300 | 1100 |
| Elongation (%) | 710 | 660 | 500 |

The sample irradiated to a dose of 10 Mrad showed significantly less spallation, when used as a peristaltic pump tubing, than Silastic Silicone Medical pump tubing.

EXAMPLE 93

A blend of Profax (17%), Kraton G2705 (78.7%) GE5530 (3%) and triallyl isocyanurate (0.3%) was melt-extruded as a tube having an internal diameter of 107 mils (0.272 cm) and an external diameter of 144 mils (0.366 cm) and was then cross-linked by irradiating it to a dosage of 5 Mrad. When tested for absorption of nitroglycerin (by a spectroscopic procedure based on U.S. Pharmacopeia XX (1980) at 410, 515 and 600 nm), this tubing had an absorption rate of 5.6 to 8.5%, as compared to absorption rates of 18% and 40% for Silastic Silicone medical tubing and PVC tubing respectively.

This formulation was also tested in the form of tubing and was found to exhibit substantially less spallation (e.g. about one-third as much) than Silastic Silicone, to retain satisfactory tensile strength and elongation after autoclaving (5 cycles, each 7 minutes at about 132° C.) and after heat aging, and to have good resistance to and low absorption of a wide variety of fluids used in medical procedures.

We claim:

1. A polymeric composition which comprises:
   (a) 5 to 40% of a thermoplastic polymer which is a polyolefin or a copolymer of an olefin and one or more polar comonomers,
   (b) 1 to 10% of a polymeric component consisting essentially of an interpenetrating network of a polysiloxane and a polyurethane or polyamide, the polymeric component containing 2 to 70% by weight of the polysiloxane, and at least 30% by weight of the polyurethane or polyamide, and
   (c) 55 to 94% of an elastomer having a Shore D Hardness of less than 60, said elastomer being selected from the group consisting of ionomers, styrene/butadiene copolymers, copolyester thermoplastic elastomers and amorphous polyamides,
   the amounts of components (a), (b) and (c) being by weight, based on the total weight of (a), (b) and (c).

2. A composition according to claim 1 in which the polymeric component consists essentially of 7 to 28% of polymer(a), 1 to 10% of polymer(b) and 62 to 92% of polymer (c).

3. A composition according to claim 2 in which the polymeric component consists essentially of 15 to 22% of polymer (a), 2 to 6% of polymer (b) and 72 to 83% of polymer (c).

4. A composition according to claim 1 wherein polymer (a) is polyethylene, polypropylene, or a copolymer of an olefin and one or more of vinyl acetate, ethyl acrylate, methyl acrylate, and methyl methacrylate.

5. A composition according to claim 1 wherein the polymer (b) comprises 2 to 15% by weight of the polysiloxane.

6. A composition according to claim 1, wherein the polymer (b) comprises a polyurethane derived from an aliphatic ether or an aromatic ester.

7. A composition according to claim 1, wherein the polymer (c) is a polystyrene/polybutadiene/polystyrene block copolymer.

8. A composition according to claim 1, which has been radiation cross-linked.

9. A composition according to claim 1 wherein polymer (a) is polyethylene, or polypropylene.

10. A composition according to claim 1 which has a tensile strength of 2,000 to 3,500 psi and an elongation of 500 to 650%.

11. A composition according to claim 1 which has a tensile strength of 1,000 to 2,000 psi and an elongation of at least 650%.

* * * * *